United States Patent
Amer et al.

(10) Patent No.: US 10,139,372 B1
(45) Date of Patent: Nov. 27, 2018

(54) TWO-STAGE CORROSION UNDER INSULATION DETECTION METHODOLOGY AND MODULAR VEHICLE WITH DUAL LOCOMOTION SENSORY SYSTEMS

(71) Applicant: Saudi Arabian Oil Company, Dhahran (SA)

(72) Inventors: Ayman Amer, Thuwal (SA); Ali Shehri, Thuwal (SA); Brian Parrott, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 8 days.

(21) Appl. No.: 15/600,317

(22) Filed: May 19, 2017

(51) Int. Cl.
*G01N 27/90* (2006.01)
*G01N 25/72* (2006.01)
*G01J 5/10* (2006.01)
*B64C 39/02* (2006.01)
(Continued)

(52) U.S. Cl.
CPC ........ *G01N 27/9033* (2013.01); *B64C 39/024* (2013.01); *G01J 5/10* (2013.01); *G01N 25/72* (2013.01); *G01N 27/00* (2013.01); *B64C 2201/123* (2013.01); *G01J 2005/0077* (2013.01)

(58) Field of Classification Search
USPC .......................................................... 702/38
See application file for complete search history.

(56) References Cited

U.S. PATENT DOCUMENTS

| 5,491,409 A | 2/1996 | Flora et al. |
| 6,194,902 B1 | 2/2001 | Kuo |

(Continued)

FOREIGN PATENT DOCUMENTS

| CN | 106383168 A | 2/2017 |
| DE | 202012100128 U1 | 2/2012 |

(Continued)

OTHER PUBLICATIONS

Riggs, K. et al.,"Drones Help Detect Corrosion under Insulation," Materials Performance. Retrieved from http://www.materialsperformance.com/articles/materialselectiondesign/2016/06/droneshelpdetectcorrosionunderinsulation. Jun. 7, 2016.

(Continued)

*Primary Examiner* — Paul D Lee
(74) *Attorney, Agent, or Firm* — Leason Ellis LLP (57) ABSTRACT

Methods and systems for inspecting insulated equipment for corrosion under insulation are provided. The system includes an autonomous unmanned vehicle having aerial and ground locomotive capabilities. The vehicle includes an infrared detector and a pulsed eddy current sensor. In the method, infrared waves emitted from the equipment are detected along the equipment with the infrared detector. Using the infrared detector, at least one image of an inner surface of the equipment is developed based on the detected infrared waves. At least one area that is susceptible to corrosion is determined based on the at least one image. The susceptible area is inspected with the pulsed eddy current sensor, which induces an eddy current in the inner wall of the equipment. Based on a rate of the decay in strength of the eddy current, it is determined whether corrosion exists at the susceptible area using a processor configured by code.

22 Claims, 6 Drawing Sheets

(51) Int. Cl.
  *G01N 27/00* (2006.01)
  *G01J 5/00* (2006.01)

(56) References Cited

U.S. PATENT DOCUMENTS

| | | | |
|---|---|---|---|
| 6,344,741 B1 * | 2/2002 | Giguere | G01N 17/006 324/225 |
| 6,570,379 B2 | 5/2003 | Crouzen et al. | |
| 8,596,861 B2 | 12/2013 | Kane et al. | |
| 9,091,664 B2 | 7/2015 | Krause et al. | |
| 9,518,918 B2 | 12/2016 | Mann | |
| 2004/0130322 A1 * | 7/2004 | Crouzen | G01B 7/10 324/229 |
| 2010/0107767 A1 | 5/2010 | Kane et al. | |
| 2015/0148955 A1 | 5/2015 | Chin et al. | |

FOREIGN PATENT DOCUMENTS

| | | |
|---|---|---|
| ES | 2572181 A1 | 5/2016 |
| WO | 2012013878 A1 | 2/2012 |
| WO | WO2016/057165 | 4/2016 |

OTHER PUBLICATIONS

Jones, R., "Use of Microwaves for the Detection of Corrosion under Insulation," Department of Mechanical Engineering. Imperial College London. Apr. 2012.

International Search Report and Written Opinion in corresponding International Patent Application No. PCT/US2018/028090, dated Jul. 25, 2018. 15 pages.

Safizadeh et al. "Gas pipeline corrosion mapping using pulsed eddy current technique." International Journal of Advanced Design and Manufacturing Technology 5.1 (2011): 11.

Beardsley, P. et. al., "VertiGo—A Wall-Climbing Robot including Ground-Wall Transition," Disney Research. Dec. 29, 2015. Retrieved from https://www.disneyresearch.com/publication/vertigo/.

B-Unstoppable, World First TankCopter. Retrieved from https://www.indiegogo.com/projects/b-unstoppable-world-s-first-tankcopter-drone-gadget-technology#/ . (2015).

'B' the Flying car. Retrieved from https://www.kickstarter.com/projects/2017062404/b-go-beyond/description . May 2013.

* cited by examiner

TWO-STAGE CORROSION UNDER INSULATION DETECTION METHODOLOGY AND MODULAR VEHICLE WITH DUAL LOCOMOTION SENSORY SYSTEMS

FIELD OF THE INVENTION

The present invention relates to a system and process for inspecting equipment for corrosion, and, more specifically, relates to nondestructive testing systems and methods for evaluating insulated equipment for corrosion under insulation and to vehicles including unmanned, autonomous, modular vehicles with dual locomotion (e.g., aerial and crawling) capabilities and dual sensory systems.

BACKGROUND OF THE INVENTION

Corrosion under insulation (CUI) is a particular type of corrosion that can occur in insulated equipment (e.g., piping) due to ingress of water into the insulated layer and moisture build-up on the external surface of the insulated equipment. Insulated equipment that is exposed to mist and cooling water towers, as well as equipment that is exposed to steam vents can be especially vulnerable to the development of CUI. CUI is difficult to detect in its early stages as its precursor is merely the accumulation of moisture and water patches underneath the insulation layers, which is not visible from outside of the equipment. CUI that remains undetected can cause major damage to the equipment and, in severe cases, can even result in the closure of a process unit that features the damaged equipment.

For insulated pipes, the structure of the pipe generally includes several layers, including (starting from the inside and moving outward): a compatible coating, the insulation material, and a metal jacket cladding. The cladding acts as a protective barrier on the outside of the piping, protecting the pipe from the outside elements (e.g., weather). For example, the cladding helps to prevent the insulation from being exposed to rain or physical damages.

Conventionally, in order to inspect insulated equipment for CUI, the portion of the equipment to be inspected is stripped of its cladding and its insulation, and is then visually inspected to see if CUI exists. These current practices, however, are time consuming and costly. Specifically, downtime of the insulated equipment during inspection, replacement of cladding after inspection, and repairs to damaged equipment (e.g., removing damaged insulation) all result in increased costs. Early detection of CUI can limit the damage to the equipment and thus limit the economic effects of the damage; however, early detection of CUI is difficult due to the time-consuming nature of the current inspection processes and the hidden nature of the precursors of CUI. Accordingly, there is a need for a more time-effective and cost-effective process for inspecting insulated equipment for CUI and its precursors. The present invention addresses one or more of these and other needs.

SUMMARY OF THE INVENTION

According to an aspect of the present invention, systems for inspecting insulated equipment for corrosion under insulation are provided. In a first aspect, a system for inspection of insulated equipment includes at least one inspection device. In at least one implementation, the at least one inspection device is an autonomous, modular unmanned vehicle having aerial and ground locomotive capabilities. According to one aspect, the vehicle includes a controller having a memory storing instructions in the form of code and a processor configured by executing the instructions therein, such that the controller is configured to enable operations of the vehicle. According to another aspect, the vehicle can also include a power source, such as a battery, configured to power all components of the vehicle. According to another aspect, the vehicle can include a power receiver operatively connected to the power source (e.g., battery). According to a further aspect, the power receiver is configured to wirelessly transfer power from a remote power source to the battery. According to one aspect, the vehicle can include at least one of an infrared module and a pulsed eddy current (PEC) module. The infrared module includes an infrared detector configured to detect infrared waves emitted from the insulated equipment and to develop an image of the inner surface of the insulated equipment at one or more locations based on the detected infrared waves. The PEC module includes at least one PEC sensor configured to induce an eddy current in the inner wall of the insulated equipment and to monitor a decay in strength of the eddy current over time. Both the infrared module and the PEC module are selectively removable from the vehicle. According to another aspect, the vehicle of the system can include a clamping mechanism configured to selectively attach the vehicle to the insulated equipment. According to another aspect, the vehicle can include at least one pair of wheels configured to move the vehicle along an outer surface of the equipment. According to a further aspect, the at least one pair of wheels are configured to move the vehicle longitudinally along the outer surface of the insulated equipment. According to another aspect, the at least one pair of wheels are omniwheels configured to enable omnidirectional locomotion along the outer surface of the insulated equipment.

According to a further aspect, the vehicle can include at least one of an infrared gas detector, a positioning module, a depth sensor, an inertia measurement unit, and a LIDAR device.

According to another aspect, the system can further include a control station having a power source and a power transmitter. The power transmitter is configured to wirelessly transfer power from the power source to the power receiver of the at least one vehicle.

According to a further aspect, the system can include two vehicles—a first vehicle comprising the infrared module and a second vehicle comprising the PEC module.

According to another aspect, a method for detecting corrosion under insulation within insulated equipment is provided. According to one aspect, at least one device comprising an infrared detector and at least one pulsed eddy current (PEC) sensor is used to perform the method. In the method, infrared waves emitted from the insulated equipment are detected with the infrared detector at one or more locations along the insulated equipment. At least one image of an inner surface of the insulated equipment at the one or more locations are developed using the infrared waves detected by the infrared detector. At least one area that is susceptible to corrosion under insulation is determined based on the at least one developed image using a processor configured by code. Positioning data corresponding to the at least one susceptible area is stored in a database of the device. According to one aspect, the positioning data is global positioning data. According to another aspect, the positioning data is relative positioning data. The device is then returned to the at least one susceptible area based on the stored positioning data. The at least one susceptible area on the insulated equipment is then inspected with the at least one PEC sensor. According to one aspect, in the inspection of the susceptible area with the at least one PEC sensor, a magnetic field is generated and the metallic jacket of the insulated equipment is penetrated with the generated magnetic field to magnetize an inner wall of the equipment, and thereby induced an eddy current in the inner wall. Further, a decay in strength of the eddy current over time is monitored and, based on a rate of the decay in strength of the eddy current, it is determined by a processor configured by code whether any corrosion under insulation exists at the at least one susceptible area.

According to another aspect of the method, the at least one device is an unmanned aerial vehicle. According to a further aspect, the unmanned aerial vehicle includes aerial and ground locomotive capabilities. According to a further aspect, an infrared module is installed on the at least one unmanned aerial vehicle, the infrared module including the infrared detector. According to a further aspect, a pulsed eddy current (PEC) module is installed on the at least one unmanned aerial vehicle, the PEC module including the at least one PEC sensor. According to another aspect, in order to install the PEC module, the infrared module is uninstalled.

According to another aspect, an infrared gas module is installed on the at least one unmanned aerial vehicle, the infrared gas module including an infrared gas detector. According to a further aspect, at least one location on the insulated equipment is tested for gas emissions indicative of corrosion under insulation using the infrared gas detector.

According to a further aspect, the unmanned aerial vehicle is positioned on the insulated equipment for inspection of the insulated equipment. According to a further aspect, in positioning the unmanned aerial vehicle on the insulated equipment, the unmanned aerial vehicle attached to the insulated equipment via a clamping mechanism housed on the unmanned aerial vehicle.

According to another aspect of the method, the one or more locations along the insulated equipment are tested, using an infrared gas detector operatively connected to the device, for gas emissions indicative of corrosion under insulation.

According to another aspect of the method, the at least one device is selected from the group consisting of an unmanned aerial vehicle, a control station, a mobile robot, and a handheld device. According to another aspect of the method, a quiescent period can be implemented after detection of the insulated equipment with the infrared detector and prior to inspection of the susceptible area with the at least one PEC sensor.

These and other aspects, features, and advantages of the present systems and methods can be appreciated from the accompanying description of certain embodiments of the invention and the accompanying drawings and claims.

DETAILED DESCRIPTION CERTAIN OF EMBODIMENTS OF THE INVENTION

By way of overview and introduction, the present disclosure details systems and methods for inspection of insulated equipment and detection of corrosion under insulation (CUI) in insulated equipment. Despite the understanding in the field that CUI can cause immense damage to insulated equipment, conventional processes for identifying areas of the equipment damaged by CUI are time-consuming and costly due to the inability to quickly and accurately identify the damaged areas. As such, in an effort to improve the efficiency and cost-effectiveness of inspection, the systems and methods as described herein provide a series of operations in which insulated equipment is assessed for possible CUI damage.

More specifically, in accordance with at least one embodiment of the present application, a system is provided for inspection of insulated equipment. The system can include one or more inspection devices (e.g., a modular, unmanned aerial vehicle ("UAV")), each of which can include one or more modules that are selectively installed on the device and used to inspect insulated equipment using various inspection techniques. In particular, the inspection device can include an infrared module that includes at least one infrared detector. The infrared detector is used to detect infrared waves transmitted from the insulated equipment, and to develop at least one infrared image of the insulated equipment based on the detected infrared waves. The infrared image can then be used to determine by a processor configured by code which areas of the insulated equipment (if any) are susceptible to CUI.

The inspection device can also include a pulsed eddy current (PEC) module that includes one or more PEC sensors. The one or more PEC sensors are configured to induce an eddy current within the inner wall of the insulated equipment at the areas of the equipment deemed susceptible to CUI based on the infrared imaging. The one or more PEC sensors can then monitor the decay of strength of the eddy current at the susceptible areas over time. The measurements regarding the decay of strength of the eddy current can then be used to determine, using a processor configured by code, whether CUI exists at the susceptible areas along the equipment.

In implementations in which the inspection device is a UAV, the inspection device can include aerial and ground locomotive capabilities such that it can be flown (e.g., controlled by a remote user) to a location on the equipment to be inspected, and can subsequently travel along the surface of the equipment (e.g., via wheels) to other inspection locations. The UAV can also include a clamping (perching) mechanism that is configured to selectively attach the UAV to the surface of the equipment and to maintain its attachment to the equipment while the UAV travels along the surface of the equipment. The clamping mechanism can be a passive mechanism that uses a minimal amount of power, which allows the UAV to conserve power for its inspection functions. For instance, the clamping mechanism can comprise a mechanical arrangement on the UAV that moves between engaged and disengaged positions solely mechanically, or with an electromechanical trigger to cause either engagement of the equipment, disengagement of the equipment, or both.

As such, the following detailed description is directed to systems and methods for detecting corrosion in insulated equipment using these systems. While the following detailed description describes, in part, methods for inspecting equipment for CUI, it should be understood that these methods can also be used to inspect equipment for other types of corrosion or damage, such as leaks or other water damage. The referenced systems and methods are now described more fully in reference to the accompanying drawings, in which one or more illustrated embodiments and/or arrangements of the systems and methods are shown. The systems and methods are not limited in any way to illustrated embodiments and/or arrangements as the illustrated embodiments and/or arrangements described herein are merely exemplary of the present systems and methods, which can be embodied in various forms as appreciated by those skilled in the art. Thus, it should be understood that any structural and functional details disclosed herein are not to be interpreted as limiting the present systems and methods, but rather are provided herein as representative embodiments and/or arrangements for teaching a person of skill in the art one or more ways to implement the present systems and methods.

Accordingly, aspects of the present systems and methods can take the form of an entirely hardware embodiment, or an embodiment combining software (including firmware, resident software, micro-code, etc.) and hardware. One of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer. Furthermore, the terms and phrases used herein are not intended to be limiting, but rather, are to provide an understandable description of the systems and methods.

Figure 1A:
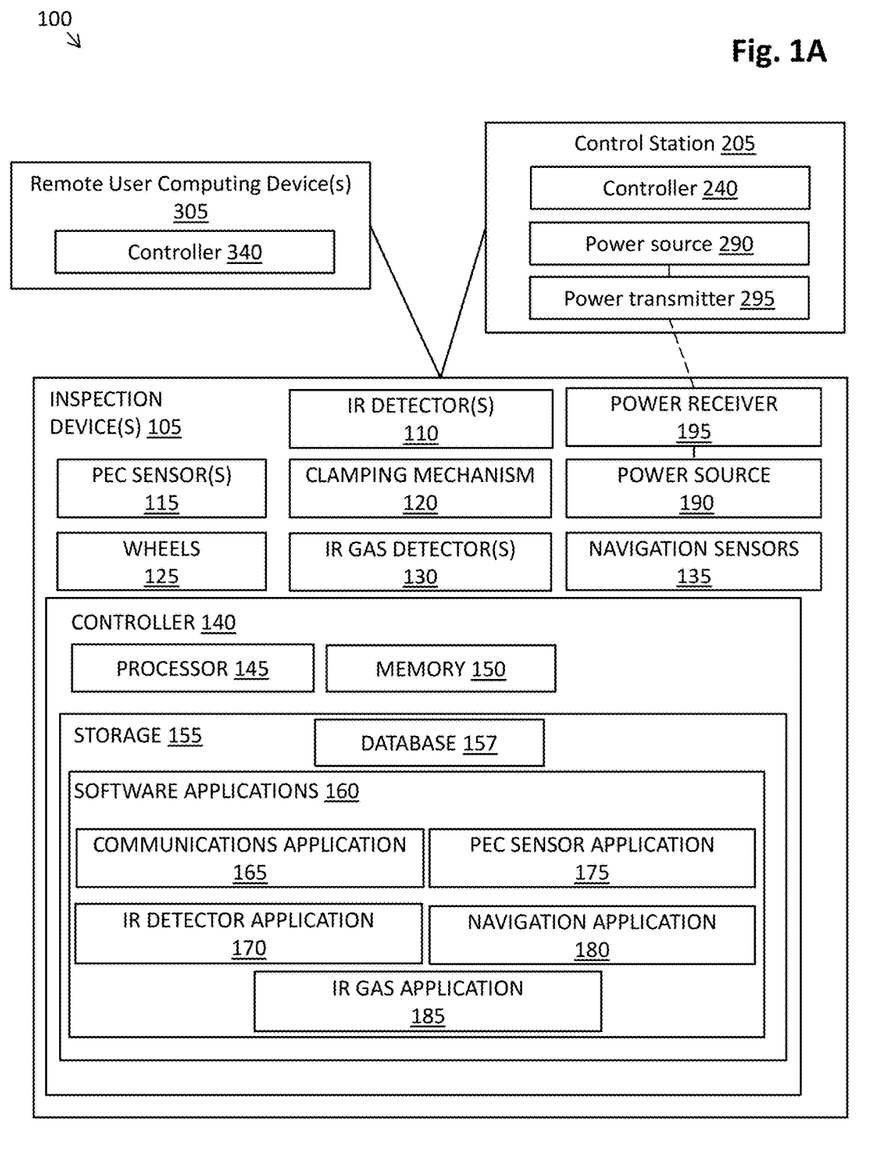
FIG. 1A is a block diagram illustrating an example configuration of a system for inspection of insulated equipment for corrosion under insulation in accordance with one or more embodiments.
Figure 1B:
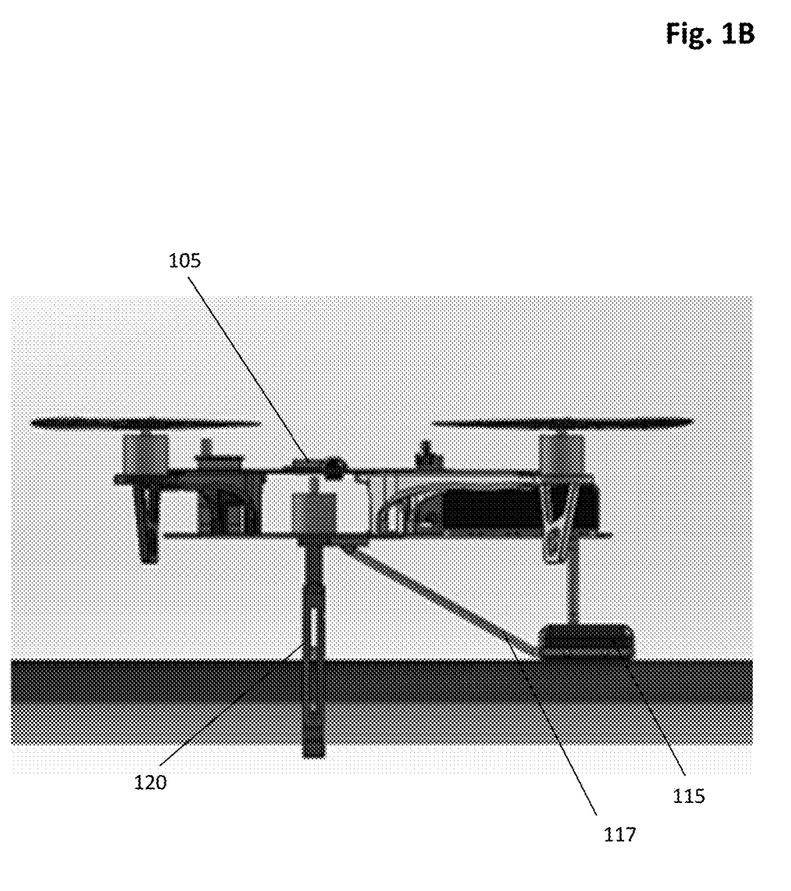
FIG. 1B is a diagram of an exemplary inspection device for inspecting insulated equipment for corrosion under insulation in accordance with one or more embodiments.

An exemplary system 100 for inspection of equipment for corrosion under insulation, in accordance with one or more embodiments, is shown at FIG. 1A. Specifically, FIG. 1A shows a block diagram illustrating an example configuration of the system 100 for inspection of equipment for corrosion, the system 100 including an inspection device 105 in accordance with one or more embodiments. FIG. 1B shows an implementation of the inspection device 105, where the inspection device 105 is a modular UAV.

As shown in FIG. 1A, the system 100 can include at least one inspection device 105. In one or more embodiments, the inspection device 105 is a UAV. In certain embodiments, the inspection device 105 can be a control station, a mobile robot (e.g., crawling robot), and/or a handheld device. In one or more implementations, the at least one inspection device 105 can include multiple inspection devices of the same or different types. For example, in at least one implementation, the system 100 can include two inspection devices 105, one of which is a UAV, and one of which is a crawling robot. Further, in another implementation, the system 100 can include two inspection devices 105, where both inspection devices are UAVs. In at least one embodiment, at least one of the inspection devices 105 can be a crawling robot for accessing areas that cannot be accessed via a UAV (e.g., areas that a UAV cannot land).

As discussed in detail below, the at least one inspection device 105 includes several features configured to enable inspection of the insulated equipment. From the diagram of FIG. 1A, it should be understood that while all of the components are shown within one device 105, in certain embodiments, the various components of the at least one inspection device 105 can be housed on separate inspection devices, such that each inspection device does not necessarily include all of the inspection components. For instance, in at least one implementation, a first inspection device can be used for infrared wave detection, while a second inspection device can be used for pulsed eddy current inspection. As such, in this implementation, the first inspection device can house at least one infrared detector, but not a pulsed eddy current sensor, while the second inspection device can house at least one pulsed eddy current sensor, but not an infrared detector.

In one or more embodiments, the at least one inspection device 105 can comprise at least one infrared (IR) detector 110 and at least one pulsed eddy current (PEC) sensor 115. In one or more implementations, the IR detector 110 and the PEC sensor 115 can be housed within respective modules that can be selectively installed on the inspection device(s) 105. In embodiments in which the inspection device 105 is a UAV, the IR detector 110 and/or the PEC sensor 115 can be installed on a tail 117 (see FIG. 1B) that acts as supporting beam and a carrier for the detector 110 and/or sensor 115. In embodiments in which the IR detector 110 and the PEC sensor 115 are housed in modules that are selectively installed in (and removed from) the inspection device 105, the IR detector (module) 110, for example, can be removed from inspection device 105 prior to installation of the PEC sensor (module) 115. Having only one module installed at a time on the inspection device 105 (as opposed to both modules) allows the inspective device 105 to conserve power. Additionally, in embodiments in which the inspection device 105 is a UAV, having only one module installed at a time decreases the weight of the UAV, which in turn provides additional power savings to the UAV during locomotion. In one or more embodiments, the modules can be installed (or uninstalled) by an operator of the inspection device 105.

The IR detector 110 is used for the first phase of inspection on the insulated equipment, which is an initial screening phase in which the system determines, using by a processor configured by code, areas along the insulated equipment that are susceptible to corrosion (e.g., CUI). More specifically, the IR detector 110 can be configured to detect infrared waves emitted from the insulated equipment during the inspection process. The IR detector 110 also comprises a camera that is configured to develop an image of the insulated equipment at the inspection location based on the detected infrared waves (i.e., infrared thermography). The infrared image can then be used to determine, using by a processor configured by code, which areas of the insulated equipment (if any) are susceptible to CUI. In general, during testing of the insulated equipment with at least one IR detector 110, the IR detector 110 is at a distance from the insulated equipment and thus is not in contact with the insulated equipment. In one or more exemplary implementations, the IR detector 110 can be a camera from FLIR Systems, Inc. of Wilsonville, Oreg. or a camera from Workswell® s.r.o. of Prague, Czech Republic. In certain implementations, the inspection device 105 having the IR detector 110 can be a stationary device (e.g., control station) or a mobile robot (e.g., crawling robot) such that the infrared detection is conducted from the ground at a distance from the insulated equipment.

In general, infrared waves (infrared radiation) are emitted by all objects (e.g., insulated equipment), with the amount of radiation emitted increasing as the temperature of the object increases. Accordingly, an IR detector/camera 110 can produce an image of an object, in conjunction with a processor configured by code implemented therein, based on the detected differences in temperature between the object and its background (i.e., the object and the background in the image are shown in different colors based on their temperature difference). Thus, in implementations in which the insulated equipment and its background have similar temperatures, an energy source (heat source) can be used to increase the temperature of the insulated equipment and, consequently, increase the radiation emitted by the object relative to its surroundings. The image produced by the IR detector/camera 110 can distinguish not only between the object and its background based on the detected radiation of each, but can also distinguish the differences between different portions of the object based on the contrasting radiation.

In the present system 100, the IR detector 110 detects the radiation emitted from the equipment and its background, and then develops at least one image, in conjunction with a processor configured by code implemented therein, based on the differences in emitted radiation between the equipment and its background. Moisture formed in the backside of the insulation material gains (and loses) heat at different rates relative to the rest of the equipment, and thus emits radiation at different levels than other areas on the equipment where moisture or CUI is not present. As such, the developed infrared image(s) can also show differences not only between the equipment and its background, but also between different portions of the equipment based on the contrasting radiation. In one or more embodiments, the infrared image can be a thermal 2-dimensional (2D) image. In at least one embodiment, such as when the inspection device 105 is a UAV, the infrared image can be a thermal 3-dimensional (3D) image (e.g., generated from point clouds captured in real time).

It should be noted that sun exposure can cause small moisture patches in the insulation material to evaporate quickly, thereby making it difficult to detect small areas of moisture accumulation in the insulation via infrared imaging. Accordingly, in implementations in which the insulated equipment is outside, IR detector inspections of the insulated equipment can be scheduled for times when evaporation due to sun exposure is unlikely to significantly affect the infrared detection and imaging, such as during the early morning or at night.

Accordingly, the IR detector 110 allows for fast and efficient determination of which areas on the insulated equipment are susceptible to corrosion. In particular, in embodiments in which the inspection device is a UAV, the attached IR detector 110 allows for safe and fast scanning of large areas along the equipment without the need for any scaffolding structures along the equipment. As such, once the susceptible areas are identified, an efficient inspection of those susceptible areas can be conducted using the at least one PEC sensor 115 to determine, using by a processor configured by code, whether corrosion (e.g., CUI) indeed exists in the susceptible areas. Further, the use of a UAV inspection device facilitates efficient inspection of hard to reach areas on the insulated equipment.

The at least one PEC sensor 115 is used for the second phase of inspection on the insulated equipment, which is the inspection of the predefined areas along the insulated equipment that were determined (via the IR detector 110) to be susceptible to corrosion. As mentioned above, the at least one PEC sensor 115 is configured to induce an eddy current within the inner wall of the insulated equipment at the selected areas of the equipment. In one or more implementations, during inspection of the insulated equipment with at least one PEC sensor 115, the at least one PEC sensor 115 is in contact with the insulated equipment. The one or more PEC sensors 115 then monitor the decay of strength of the eddy current at the susceptible areas over time. The decay of strength measurements are then used to determine, using by a processor configured by code, whether corrosion (e.g., CUI) exists at the susceptible areas along the equipment. In one or more exemplary implementations, the at least one PEC sensor 115 can be one of several sensors available from Eddyfi® of Québec, Canada.

The at least one PEC sensor 115 is based on induced electromotive force loops as a result of varying magnetic field-propagating conductive materials. The resultant magnetic loops resemble water currents and produce their own magnetic fields that can be detected in the insulated material using one or more coil sensors probe coils. The presence of crack defects and/or water patches within the insulation of the equipment disturb the eddy current propagation, thereby reducing the strength of the eddy current and increasing the coil sensor impedance.

In structure, the PEC sensor 115 generally comprises a probe coil and the sensor 115 is configured to generate an electric current (primary current), which generates a magnetic field (primary field) in the probe coil. The magnetic field (primary field) then penetrates the metal jacket of the insulated equipment at the inspection location to magnetize the pipe wall, thereby inducing an eddy current in the pipe wall. The eddy current diffuses inwardly and gradually decreases (decays) in strength (e.g., as it encounters defects in the equipment). The sensor 115, and in particular the probe coil of the sensors 115, can be configured to monitor the decay in strength of the eddy current over time. The thickness of the inspected equipment is correlated to the length of time it takes for the eddy current to indicate a change in the decay rate. In other words, the change in decay rate of the eddy current can be used to determine, using by a processor configured by code, whether the thickness of the insulated equipment has changed at an inspection location, which is an indication of corrosion at that location.

In one or more alternative embodiments, other types of sensors can be used in place of the PEC sensor to inspect susceptible areas along the pipeline, such as an electromagnetic acoustic transducer (EMAT) or an alternating current field measurement (ACFM) sensor.

With reference to FIGS. 1A-B, in embodiments in which the inspection device(s) 105 is a UAV, the inspection device 105 can further include a clamping mechanism 120 configured to selectively attach the UAV to the insulated equipment during inspection and testing of the equipment. In an exemplary embodiment shown at FIG. 2A, the clamping mechanism 120 can comprise two arms in a C-shaped configuration that are configured, using a motor, to wrap around the insulated equipment (e.g., pipe) and selective hold onto (attach to) the equipment via tension. In this embodiment, the clamping mechanism 120 can be a passive mechanism in that the two arms open and hug around the pipe when the arms approach the pipe without the need for additional motors. This type of passive mechanism minimizes the power consumption needed for attaching the UAV to the insulation equipment, thereby allowing the UAV to conserve power for its inspection functions. In at least one implementation, the clamping mechanism can comprise a mechanical arrangement on the UAV that moves between engaged and disengaged positions solely mechanically, or with an electromechanical trigger to cause either engagement of the equipment, disengagement of the equipment, or both.

Figure 2A:
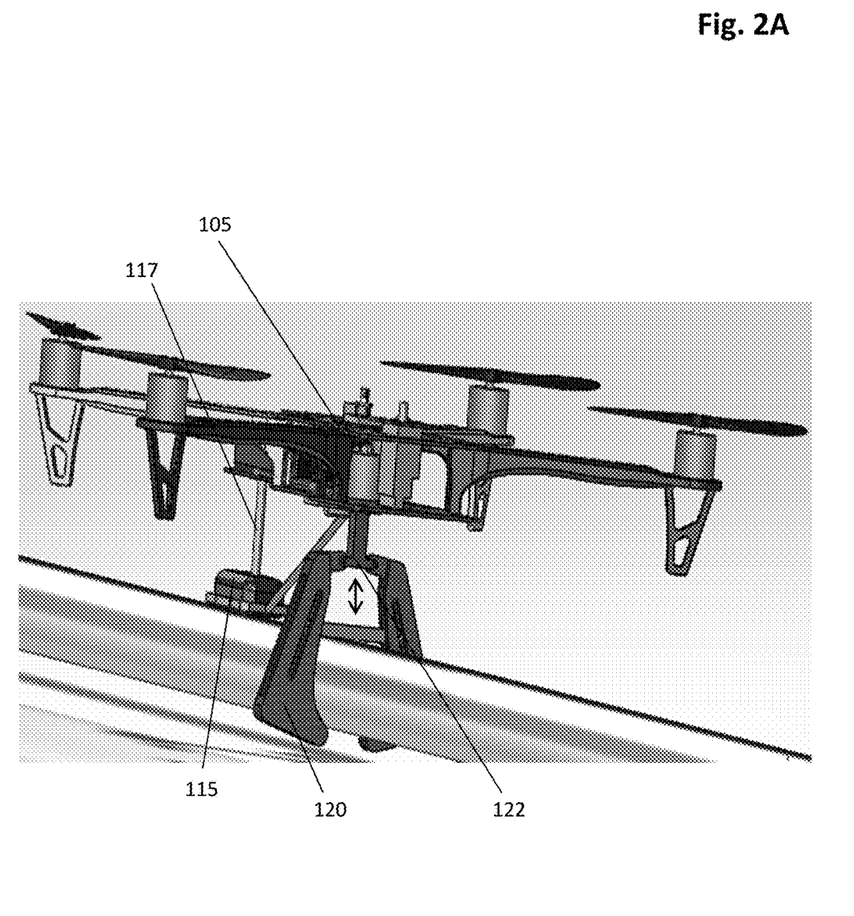
FIG. 2A is a diagram of an exemplary inspection device having a clamping mechanism for selectively attaching to the insulated equipment during the inspection process in accordance with one or more embodiments.

With continued reference to FIG. 2A, in one or more implementations, the clamping mechanism 120 can include a spring, screw, and rock gear configuration 122. In this embodiment, the spring is attached to the screw and both are attached to the framework (truss) of the UAV. As such, when the UAV approaches the targeted equipment (e.g., pipe), the screw is pushed up, causing the truss to rotate and lock the clamp around the equipment. For unlocking the clamping mechanism, when the UAV is moving upward away from the equipment, a downward force is exerted on the screw causing the truss to rotate back to an "unlock" position such that the clamping mechanism opened and the drone detaches from the equipment.

Figure 2B:
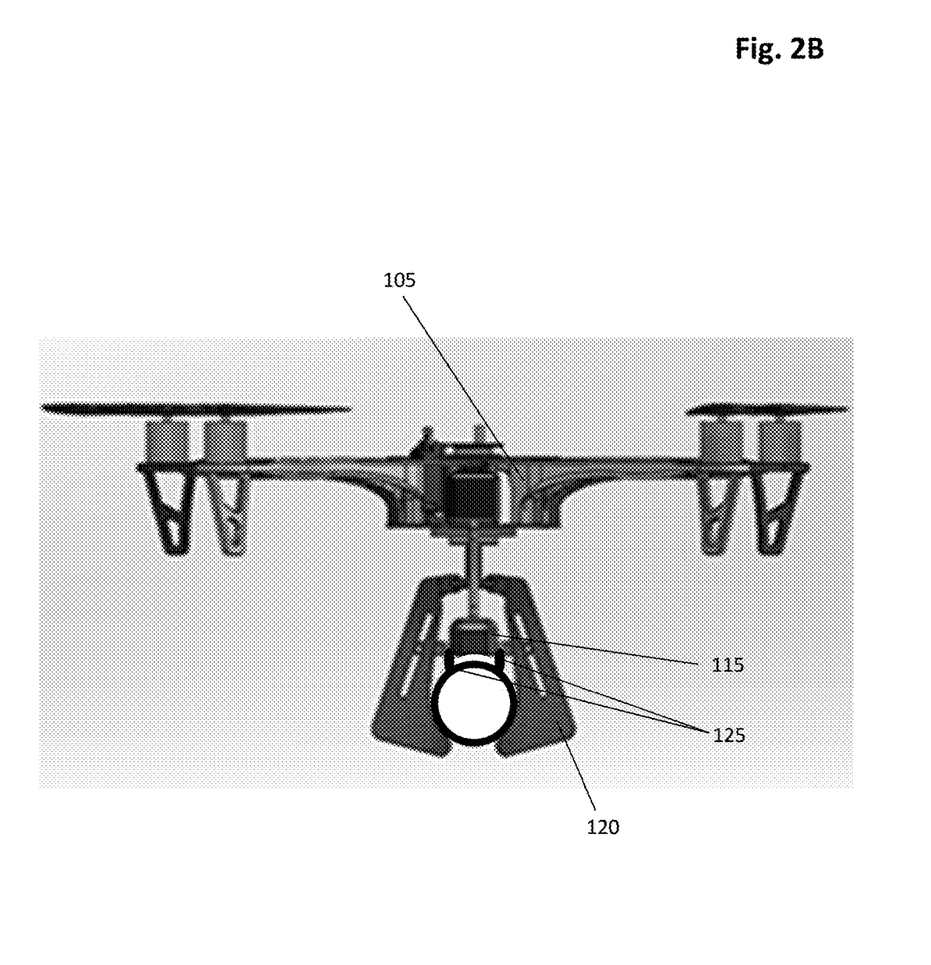
FIG. 2B is a diagram of an exemplary inspection device having wheels for moving the inspection device 105 along the outer surface of the insulated equipment in accordance with one or more embodiments.

Referring now to FIG. 2B (and FIG. 1A), in one or more embodiments, such as when the inspection device 105 is a UAV, the inspection device can also include at least one pair of wheels 125 that are configured to move the inspection device 105 along the outer surface of the equipment. For instance, in one or more implementations such as the embodiment of FIG. 2B, the wheels 125 can contact the surface of the equipment when the UAV is attached to the equipment via the clamping mechanism 120. While the embodiment of FIG. 2B shows the wheels 125 attached to the housing of the PEC sensor (module) 115, it should be appreciated that in other implementations, the wheels can be attached to another portion of the inspection device 105 that is configured to come into contact with the surface of the equipment. For example, in at least one embodiment, the wheels 125 can be located on the clamping mechanism. In one or more implementations, the wheels 125 are configured to move the UAV longitudinally along the outer surface of the equipment. In at least one implementation, the wheels can be omniwheels or the like, which are configured to enable omnidirectional locomotion along the outer surface of the equipment. In one or more implementations, the UAV is configured to move along the outer surface of the equipment via the wheels 125 while simultaneously detecting the infrared waves via IR detector 110. In at least one embodiment, the inspection device(s) 105 can further include at least one infrared gas detector 130 configured to detect the presence of one or more gases associated with corrosion. In one or more implementations, the infrared gas detector 130 can be used with (or without) the IR detector 110 as part of the initial screening inspection phase. In other words, the infrared gas detector 130 can also be used to determine areas along the insulated equipment that are susceptible or vulnerable to corrosion based on the gas emitted at those areas. In one or more implementations, the infrared gas detector 130 ca be implemented on the inspection device 105 (e.g., UAV) as a module such that the infrared gas detector 130 is operatively connected to the inspection device 105. In one or more exemplary implementations, the gas detector 130 can be a FUR® gas detector.

In at least one implementation, a single detector can comprise the features of both the infrared gas detector 130 and the IR detector 110, such as those produced by FLIR®, for example. Accordingly, in certain implementations, an infrared detector module that comprises an IR detector 110 can further comprise an infrared gas detector 130.

In certain embodiments, such as when the inspection device(s) 105 is a UAV, the at least one inspection device 105 can also include one or more navigation sensors 135. The one or more navigation sensors can include a positioning module, a depth sensor, an inertia measurement unit, and/or a LIDAR device. One or more of the navigator sensor 135 can be used to maneuver the inspection device 105 into position to inspect the insulated equipment and/or attach to the insulated equipment (e.g., via clamping mechanism 120. Further, the positioning module can be configured to define an area deem susceptible to CUI after analysis of the infrared image ("susceptible area"), such that the inspection device 105 can readily return to the susceptible areas for inspection via the PEC sensor 115.

More specifically, in one or more implementations, the positioning module can be configured to generate positioning data (e.g., coordinate data) for a susceptible area and store the positioning data in a database of the inspection device. The inspection device can then be configured to use the stored positioning data to return the inspection device to the susceptible area at a later time for the performance of additional testing (e.g., inspection with the PEC sensor). In one or more implementations, the positioning module can be configured to generate and store relative positioning data, meaning that the positioning data corresponding to a location (e.g., susceptible area) is relative to a particular origin location at or near the pipeline, such as a control station. In at least one implementation, the positioning module can be configured to generate and store global positioning data (e.g. via GPS) corresponding to a global location of an area (e.g., susceptible area) on the pipe. In at least one implementation, the positioning module can also be configured to generate positioning data for areas that are deemed not to have corrosion. This positional data can then be stored in the database such that the inspection device is configured not to return to locations that are free of corrosion.

With continued reference to FIG. 1A, in one or more embodiments, the inspection device 105 can comprise a controller 140. The controller 140 can be arranged with various hardware and software components that serve to enable various operations of the system 100, including a hardware processor 145, a memory 150, and storage 155. The processor 145 serves to execute software instructions that can be loaded into the memory 150. The processor 145 can comprise a number of processors, a multi-processor core, or some other type of processor, depending on the particular implementation. In one or more embodiments, the controller 140 can be operatively connected (e.g., wired or wireless connection) to the other components of the inspection device 105, such as the IR detector 110, the PEC sensor 115, and the infrared gas detector 130 such that the controller 140 can enable the various inspection operations of the inspection device 105.

In one or more implementations, the memory 150 and/or the storage 155 are accessible by the processor 145, thereby enabling the processor 145 to receive and execute instructions stored on the memory 150 and/or on the storage 155. The memory 150 can be, for example, a random access memory (RAM) or any other suitable volatile or non-volatile computer readable storage medium. In addition, the memory 150 can be fixed or removable. The storage 155 can take various forms, depending on the particular implementation. For example, the storage 155 can contain one or more components or devices such as a hard drive, a flash memory, a rewritable optical disk, a rewritable magnetic tape, or some combination of the above. The storage 155 also can be fixed or removable.

In one or more embodiments, at least one database 157 is stored on storage 155. As will be described in greater detail below, the database 157 contains and/or maintains various data items and elements that are utilized throughout the various operations of the present system 100 including but not limited to storing data corresponding to measurements and readings, as well as positioning data corresponding to the one or more locations (e.g., susceptible areas) along the insulated equipment at which the measurements and readings were taken. It should be noted that although database 157 is depicted as being configured locally to controller 140, in certain implementations, database 157 and/or various of the data elements stored therein can be located remotely (such as on a remote server—not shown) and connected to controller 140 through a network (e.g., Internet) in a manner known to those of ordinary skill in the art.

One or more software applications/programs 160 ("software applications 160") are encoded in the storage 155 and/or in the memory 150. The software applications 160 can comprise one or more software programs or applications having computer program code or a set of instructions executed in the processor 145. Such computer program code or instructions for carrying out operations and implementing aspects of the systems and methods disclosed herein can be written in any combination of one or more programming languages. The program code can execute entirely on the system 100, as a stand-alone software package, partly on the system 100 and partly on a remote computer/device or entirely on such remote computers/devices. In the latter scenario, the remote computer systems can be connected to system 100 through any type of network, including a local area network (LAN) or a wide area network (WAN), or the connection can be made through an external computer (for example, through the Internet using an Internet Service Provider).

In one or more embodiments, included among the software applications 160 can be a communications application 165, an IR detector application 170, a PEC sensor application 175, a navigation application 180, and an infrared gas application 185 that are executed by processor 145. During execution of the software applications 160, the processor 145 is configured to perform various operations relating to the configuration of the system 100. In addition, it should be noted that other information and/or data relevant to the operation of the present systems and methods can also be stored on the storage 155, for instance various control programs used in the configuration of the system 100.

Similarly, in an alternative embodiment, the system 100 can include a control module (in place of the controller 140) that can be arranged with various hardware and software components that serve to enable operation of the system, including a processor, a memory, an IR detector application, a PEC sensor application, a navigation application, an infrared gas application, and a computer readable storage medium in order to execute the various functions of the system 100.

With continued reference to FIG. 1A, in one or more embodiments, the inspection device 105 can comprise a power source 190 (e.g., battery). In at least one embodiment, the inspection device 105 can further comprise a power receiver 195 operatively connected to the power source 190 and configured to wirelessly transfer power from an outside power source to the power source 190. The power source 190 can also be configured to deliver power to other components of the inspection device 105, such as the IR detector 110 and the PEC sensor 115. In at least one implementation, the IR detector 110 and/or the PEC sensor 115 can have separate, respective power sources.

In one or more embodiments, the system 100 can further comprises a control station 205 having a controller 240 and a power source 290. The controller 240 can be arranged with various hardware and software components that serve to enable certain operations of the system 100, including a processor, a memory, one or more applications/programs, and a computer readable storage medium in order to execute the various functions of the system 100. In one or more embodiments, the control station 205 can wirelessly communicate with the inspection device 105, such as via radio frequency (RF) signals transmitted between transmitter/receivers of the inspection device 105 and the control station 205, respectively. For instance, command signals can be sent from transmitted from the control station 205 to the inspection device 105 which configure the processor 145 and/or other elements of the inspection device 105 to perform functions related to the inspection of the insulated equipment.

Figure 3:
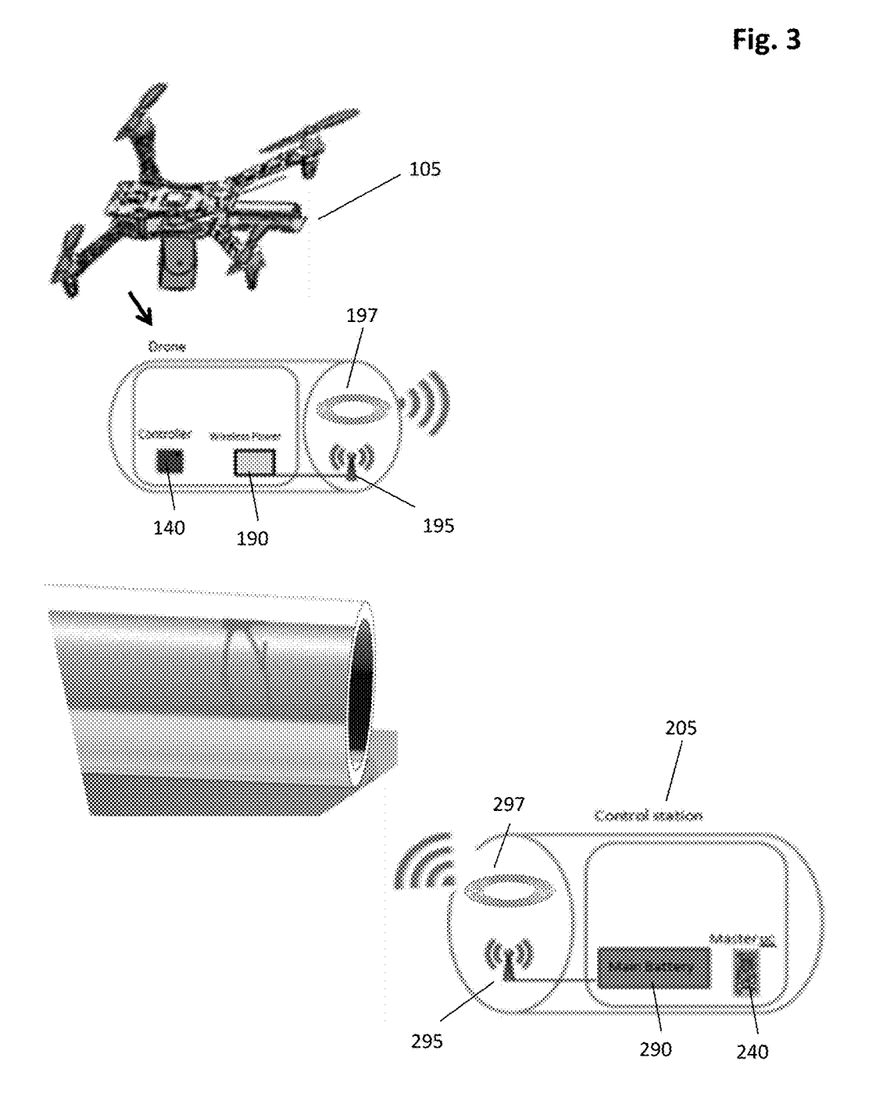
FIG. 3 is a diagram illustrating a configuration of the system for inspection of insulated equipment including an wireless power transfer configuration in accordance with one or more embodiments.

In at least one embodiment, the control station 205 can also comprise a power transmitter 295 operatively connected to the power source 290 and configured to transfer power to the inspection device 105 via power receiver 195. The power transfer from the control station 205 to the inspection device 105 can be accomplished via magnetic resonance or inductive power transfer methods. For example, FIG. 3 illustrates a wireless transfer of power from a control station 205 to an inspection device (UAV) 105 via an inductive power transfer method. In the embodiment of FIG. 3, an electrical current is transferred wirelessly from the control center 105 to the UAV (105) through the use of coils 197 and 297 to induce an electromagnetic field. These wireless power transfer methods can eliminate the use of physical connectors and cables for power transfer, and thus can provides greater efficiency, cost savings, and safety advantages over traditional power transfer via cables.

Wireless power transfer to the inspection device 105 can occur when the inspection device (e.g., UAV) has been removed from the equipment, such as in between inspections. Alternatively, wireless power transfer can occur while the inspection device 105 is attached to the insulated equipment (e.g., via clamping mechanism 120). In this implementation, the power source 290 used to transfer power to the inspection device 105 must be within a pre-specified distance from the inspection device 105 on the equipment to allow for effective wireless power transfer. Power transfer while the inspection device 105 is still on the equipment provides an added benefit of allowing the inspection device 105 to inspect greater areas of the insulated equipment at one time without having to withdraw from the equipment area.

Referring back to FIG. 1A, in one or more implementations, a user can transmit command signals or other signals to the inspection device 105 from one or more other remote user computing devices 305. More specifically, remote user computing device 305 can comprise a controller 340 that can be arranged with various hardware and software components that serve to enable certain operations of the system 100, including a processor, a memory, one or more applications/programs, and a computer readable storage medium in order to execute the various functions of the system 100. Like control station 205, user computing device 305 can wirelessly communicate with the inspection device 105 (or the control station 205), via radio frequency (RF) signals or the like transmitted between transmitter/receivers of the inspection device 105 and the user computing device 305, respectively. For instance, command signals can be sent from transmitted from the user comping device 305 to the inspection device 105 which configure the processor 145 and/or other elements of the inspection device 105 to perform functions related to the inspection of the insulated equipment. In one or more implementations data signals can also be wirelessly transmitted between the inspection device 105, the control station 205, and/or the user computing device 305, where the data signals comprise data corresponding to tests or inspections of the insulated equipment conducted by the infrared detector 110, the PEC sensor 115, and/or the infrared gas detector 130. The transmitted data can also comprise positioning data corresponding to one or more areas on the equipment at which inspections occurred or will occur.

Figure 4:
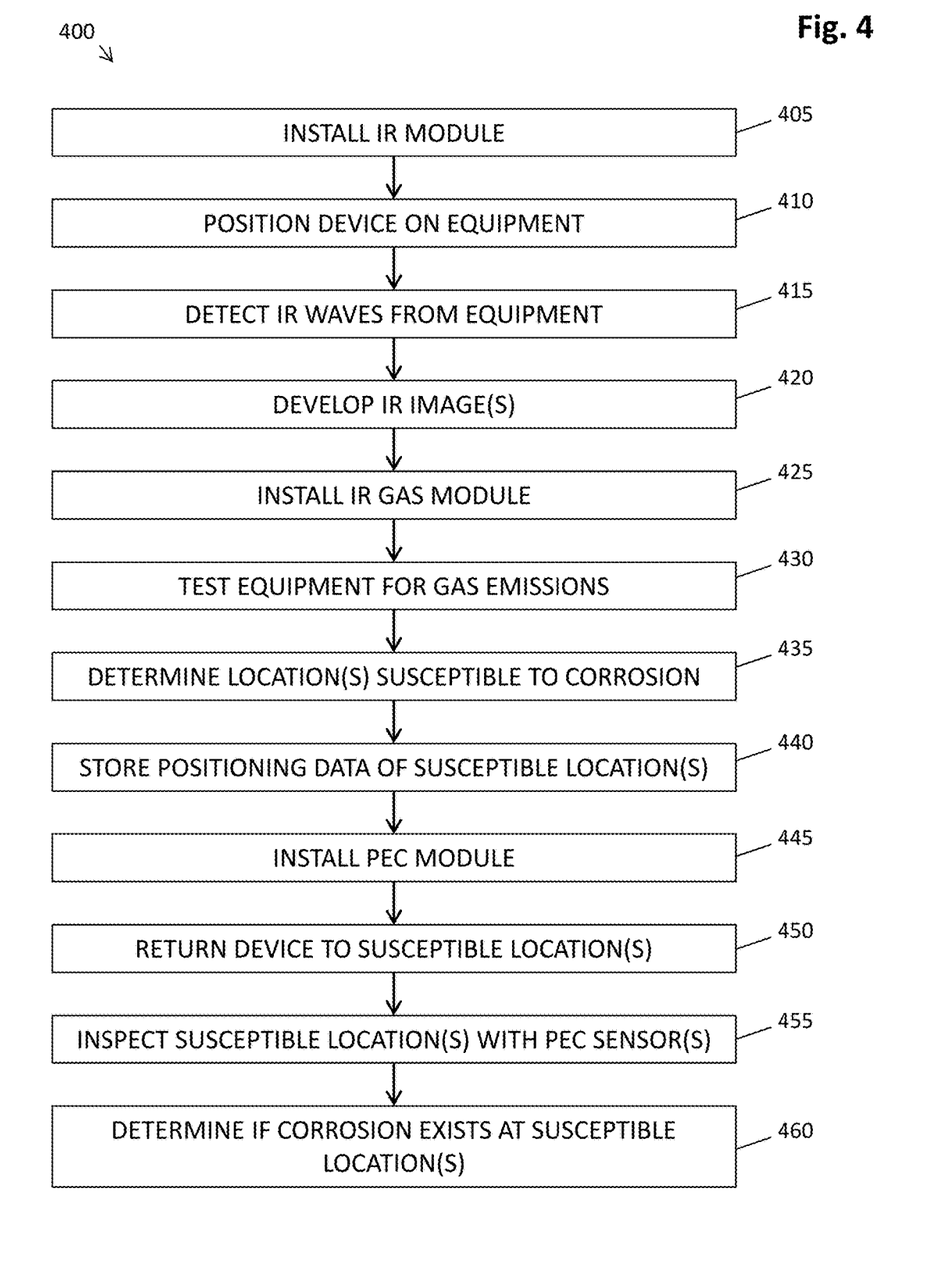
FIG. 4 is a flow diagram showing a routine that illustrates a broad aspect of a method for detecting corrosion under insulation within insulated equipment in accordance with one or more embodiments.

FIG. 4 provides a flow diagram showing a routine 400 (steps 405-460) that illustrates a broad aspect of the method for detecting CUI within insulated equipment in accordance with one or more embodiments. It should be appreciated that several of the logical operations described herein are implemented (1) as a sequence of computer implemented acts or program modules running on system 100, and/or (2) as interconnected machine logic circuits or circuit modules within the system 100. The implementation is a matter of choice dependent on the requirements of the device (e.g., size, energy, consumption, performance, etc.). Accordingly, the logical operations described herein are referred to variously as operations, steps, structural devices, acts, or modules. As referenced above, several of these operations, steps, structural devices, acts and modules can be implemented in software, in firmware, in special purpose digital logic, and any combination thereof. It should be appreciated that more or fewer operations can be performed than shown in the figures and described herein. These operations can also be performed in a different order than those described herein. Further, some operations can be performed substantially the same time as other operations.

The process begins at step 405, at which the at least one IR detector 110 is installed on the inspection device 105, for instance as an IR detector module. For example, in embodiments in which the inspection device 105 is a modular UAV, the IR detector (module) 110 is installed on the UAV (e.g., on its tail). In certain implementations, the IR detector 110 can be permanently installed on the inspection device 105. As such, in implementations in which the IR detector is a permanent component of the inspection device 105, the process begins at the next step (step 410).

At step 410, the inspection device 105 is positioned on the insulated equipment. In one or more embodiments, the inspection device 105 can be manually placed by a user at a location along the insulated equipment. In an embodiment in which the inspection device 105 is a UAV, the UAV (inspection device 105) can be remotely operated by a user and flown to a location along the insulated equipment. More particularly, a user from a remote user computing device 305 or control station 205 can transmit commands to the UAV, which configure the processor 145 and/or other elements to perform functions to fly the UAV to a location along the insulated equipment. For example, in response to one or more commands sent from a remote user computing device 305, the processor 145, executing one or more software applications 160, including preferably navigation application 180, configures the UAV (105) to fly to a location along the insulated equipment. In one or more implementations, in response to one or more commands sent from a remote device, the processor 145 executing the navigation application 180 can also configure one or more navigation sensors (e.g., a positioning module, a depth sensor, an inertia measurement unit, and/or a LIDAR device) to operate in order to guide the UAV safely and efficiently to the selected location on the insulated equipment. In one or more implementations, in response to one or more commands sent from a remote device, the processor 145 executing the navigation application 180 can also configure the clamping mechanism 120 to wrap around the insulated equipment at the selected location.

At step 415, the IR detector 110 is configured to detect infrared waves emitted from the insulated equipment. More specifically, the processor 145, executing one or more software applications, including IR detector application 170, configures the IR detector 110 to detect infrared waves emitted from the insulated equipment. In one or more implementations at step 415, particularly in implementations in which the inspective device 105 is a UAV with wheels 125, the inspection device 105 is configured to move along the insulated equipment such that the IR detector 110 can detect infrared waves at multiple locations along the insulated equipment. For example, after the clamping mechanism 120 has wrapped around the insulated equipment, the processor 145 of the UAV (inspection device 105), in response to user commands from a remote device and executing the navigation application 180, can configure the UAV to move via the wheels 125 to various locations along the outer surface of the equipment to detect infrared waves emitted from the equipment at those locations. In one or more implementations, the UAV is configured to detect the infrared waves via IR detector 110 while moving along the outer surface of the equipment via the wheels 125.

At step 420, the processor 145 executing one or more software applications 160, including IR detector application 190, is configured to develop at least one infrared image of the inner surfaces of the insulated equipment at one or more locations on the insulated equipment based on the infrared waves detected by the IR detector 110. The infrared image of the one or more selected locations on the insulated equipment can allow for the detection of potential CUI and/or water accumulation based on the varying temperatures of certain portions of the insulated equipment (shown in different colors in the infrared image) relative to other portions of the equipment. In one or more implementations, after the images on the inner surfaces of the equipment are developed with the IR detector 110, the processor 145 can be configured to store the images in database 157.

In one or more embodiments, at step 425 an infrared gas detector (module) 130 is installed on the inspection device 105. For instance, in an embodiment in which the inspection device 105 is a modular UAV, the infrared gas detector module 130 is installed on the UAV. In certain implementations, only one module can be installed on the UAV at one time. As such, in this instance, the IR detector module 110 is removed or uninstalled from the UAV before the infrared gas detector module 130 can be installed. As discussed above, having only one module installed at a time on the inspection device 105 allows the inspective device 105 to conserve power. More particularly, in embodiments in which the inspection device 105 is a UAV, having only one module installed at a time decreases the weight of the UAV, which in turn provides additional power savings for the battery of the UAV during locomotion. In one or more embodiments, the modules can be installed (or uninstalled) by an operator of the inspection device 105.

In one or more embodiments, at step 430 the infrared gas detector 130 is configured to test one or more locations along the insulated equipment for gas emissions indicative of corrosion. More specifically, the processor 145, executing one or more software applications, including infrared gas application 185, configures the infrared gas detector 130 to test one or more locations along the outer surface of the insulated equipment for gas emissions indicative of corrosion. The infrared gas detector 130 is configured to detect the presence of one or more gases associated with corrosion. In one or more implementations, the infrared gas detector 130 can be configured to test the same locations on the insulated equipment as the locations inspected by the IR detector 110 at step 415. For example, in an embodiment in which the inspection device 105 is a UAV, the UAV can be configured to test each selected location on the insulated equipment first with the IR detector 110 and then with the infrared gas detector 130, or vice versa. In at least one implementation, the infrared gas detector 130 can be configured to test different locations on the insulated equipment relative to the locations inspected with the IR detector 110. In one or more implementations, after the tests are conducted with the infrared gas detector 130, the processor 145 can be configured to record and store results of the tests in database 157.

At step 435, a determination is made as to whether locations on the equipment inspected using the IR detector 110 and/or infrared gas detector 130 are susceptible to corrosion. This determination can be based on an analysis of the developed infrared images and/or an analysis of the infrared gas detector readings. In certain implementations, the determination of step 435 can be accomplished by a processor configured by code implemented therein. Software associated with the PEC package being utilized, for instance, can be implemented in a hardware processor to make thickness determinations and provide further analyses. It should be appreciated that, in certain implementations of the method 400 an infrared gas detector 130 is not used (i.e., steps 425 and 430 do not occur), and thus the determination made at step 435 is based solely on an analysis of the developed infrared images. Likewise, in an alternative implementation of method 400, an IR detector 110 is not used (i.e., steps 405, 415, and 420 do not occur), and thus the determination made at step 435 is based solely on an analysis of the infrared gas detector readings. Further, in another alternative embodiment, the IR gas detector 130 and the IR detector 110 are both part of the IR module. Accordingly, in this alternative embodiment, the step 425 is eliminated as step 405 includes the installation of a module that comprises the IR detector 110 and the infrared gas detector 130.

At step 440, positioning data corresponding to the locations that are deemed susceptible to corrosion (susceptible locations) are generated and stored in database 157. More specifically, upon determining that a location on the equipment is susceptible to corrosion, the processor 145 can be configured to store positioning data (e.g., relative positioning data, global positioning data) identifying the location on the equipment that susceptible to corrosion in the database 157.

At step 445, one or more PEC sensors 115 are installed on the inspection device 105. For instance, in an embodiment in which the inspection device 105 is a modular UAV, the PEC sensor(s) 115 are housed in a module, and the module is installed on the UAV. As discussed above, in certain implementations only one module can be installed on the inspection device (e.g., UAV) at one time. As such, in this instance, the IR detector module 110 or infrared gas module 130 is removed or uninstalled from the UAV before the PEC sensor (module) 115 can be installed. In one or more embodiments, the PEC sensor (module) 115 can be installed (or uninstalled) by an operator of the inspection device 105.

At step 450, the inspection device 105 is returned to the one or more susceptible locations on or along the pipe for further inspection. In particular, the processor 145, executing one or more software applications, including navigation application 180, configures the inspection device 105 to return to the one or more susceptible locations based on the store positioning data corresponding to the susceptible locations. For instance, in an embodiment in which the inspection device 105 is a UAV featuring one or navigation sensors (e.g., a positioning module), the UAV is configured to returned to retrieve the stored positioning data in the database 157, and return to the susceptible location(s) corresponding to the stored positioning data. The positioning data can comprise relative positioning data (e.g., positioning data for a location that is relative to a particular origin location at or near the pipeline) and/or global positioning data (e.g., GPS data). In one or more implementations, the inspection device 105 (e.g., UAV) can be configured to return to the susceptible location(s) automatically after installation of the PEC sensor 115. In at least one implementations, the inspection device 105 can be configured to return to the susceptible locations as a result of command signals transmitted from a remote device (e.g., control station 205, remote computing device 305).

At step 455, the one or more PEC sensors 115 are configured to inspect one or more locations along the insulated equipment deemed to be susceptible to corrosion as determined at step 435. More specifically, the processor 145, executing one or more software applications, including PEC sensor application 175, configures the one or more PEC sensors 115 to inspect one or more locations along the insulated equipment that were determined to be susceptible to corrosion. In one or more implementations of step 455, particularly in implementations in which the inspective device 105 is a UAV with wheels 125, the inspection device 105 is configured to move along the insulated equipment (e.g., as a result of command signals from a remote device) such that the PEC sensors 110 can perform inspections at multiple locations along the insulated equipment. For example, after the clamping mechanism 120 has wrapped around the insulated equipment, the processor 145 of the UAV (inspection device 105), in response to user commands and executing the navigation application 180, can configure the UAV to move via the wheels 125 to the susceptible locations along equipment to inspect the equipment at those locations using the PEC sensors. In one or more implementations, the UAV can move on the outer surface of the equipment using the wheels 125 and drag the PEC sensor(s) 110 as the PEC sensor(s) 110 perform the inspection in a specific speed mode, such that specific speed of the UAV matches the dynamic scanning mode speed of the PEC sensor 110. In one or more implementations, the dynamic scanning mode for the PEC sensor 110 can reach speeds up to approximately 75 mm/s (approximately 3 inches per second). The inspection speed can be dependent upon the PEC sensor speed characteristics and its dragging scan features.

As mentioned above, the at least one PEC sensor 115 is configured to induce an eddy current within the inner wall of the insulated equipment at each susceptible location on the insulated equipment. The one or more PEC sensors 115 then monitor the decay of strength of the eddy current at each susceptible location over time. The decay of strength measurements are then used to determine, using by a processor configured by code, whether corrosion (e.g., CUI) exists at the susceptible location at step 460, as discussed below. In one or more implementations, after the inspection with the PEC sensors, the processor 145 can be configured to store the measurements (e.g., decay of strength measurements) of the PEC sensors in database 157.

In one or more implementations, a quiescent period can occur between testing of the equipment with the IR detector 110 (and/or infrared gas detector 130) and inspection with the PEC sensor 115. In particular, a quiescent period can be utilized as a preparation period for the second phase inspection (using the PEC sensor 115) after targeting predefined susceptible areas detected by the IR detector 110 (the first inspection phase). In the implementations in which a quiescent period is used, the quiescent period is a finite period for example, 1 second, 1 to 5 seconds, 1 to 10 seconds, 1 to 15 seconds, 1 to 30 seconds, or 1 second to 1 minute. In one or more implementations, the quiescent period can overlap with and/or occur at substantial the same time as steps 435, 440, 445, and/or 450.

At step 460, a determination is made as to whether corrosion exists at the susceptible locations on the insulated equipment. This determination can be based on an analysis of the decay of strength measurements recorded by the one or more PEC sensor 115 during inspection of each susceptible location. For example, the results of the decay of strength of the eddy current measurements can be used to determine, using by a processor configured by code, the thickness of the inner wall and the size of the defect in the wall (if any). Decay of strength measurements that indicate a decreased in wall thickness can signify corrosion at that location. In one or more implementations, the processor is calibrated to determine decreases in wall thickness in the insulated equipment based on wall thickness measurements and corresponding decay of strength measurements for a reference sample or a tested surface. Based on variations between the collected decay of strength data from the insulated equipment and that corresponding data for the reference sample, the processor can be configured to determine whether anomalies linked to wall loss and/or wall thinning of the insulated equipment are present. In one or more implementations, upon determining that corrosion under insulation exists at a location on the equipment, the processor 145 can be configured to store data identifying the corrosion location on the equipment in the database 157.

In at least one implementation, the above described method can be completed using two or more inspection devices such as two or more UAVs. For example, in at least one implementation, a first UAV can comprise an IR detector (or an IR detector module featuring an IR detector), which can be configured to develop one or more infrared images of the insulated equipment and thus identify potential trouble areas (i.e., areas susceptible to corrosion). In certain implementations, the first UAV can further comprise an infrared gas detector (and/or an infrared gas module featuring an infrared gas detector) for detecting gas along the equipment that is indicative of CUI. Subsequently, a second UAV comprising a PEC sensor (or a PEC module featuring a PEC sensor) can be configured to inspect the equipment at the areas deemed susceptible to CUI for determining whether CUI exists at the susceptible areas of the equipment. In certain implementations, the dispatch of the first UAV and the second UAV can overlap such that the second UAV can inspect identified susceptible locations, while the first UAV continues to scan the equipment to determine, using by a processor configured by code, other susceptible areas, thereby leading to shorter inspection times.

In at least one implementation, multiple UAVs can be used to perform the infrared wave detections and/or infrared gas detection, and multiple UAVs can be used to perform inspection of susceptible areas with a PEC sensor. The use of multiple UAVs to perform the various tasks of the present method can increased the speed of inspection, particular for large areas of insulated equipment.

It should be understood that although much of the foregoing description has been directed to systems and methods for inspecting insulated equipment for corrosion, the system and methods disclosed herein can be similarly deployed and/or implemented in scenarios, situations, and settings far beyond the referenced scenarios (e.g., inspection of the insulated equipment for other types of damage). It should be further understood that any such implementation and/or deployment is within the scope of the system and methods described herein.

It is to be understood that like numerals in the drawings represent like elements through the several figures, and that not all components and/or steps described and illustrated with reference to the figures are required for all embodiments or arrangements. It should also be understood that the embodiments, implementations, and/or arrangements of the systems and methods disclosed herein can be incorporated as a software algorithm, application, program, module, or code residing in hardware, firmware and/or on a computer useable medium (including software modules and browser plug-ins) that can be executed in a processor of a computer system or a computing device to configure the processor and/or other elements to perform the functions and/or operations described herein. It should be appreciated that according to at least one embodiment, one or more computer programs, modules, and/or applications that when executed perform methods of the present disclosure need not reside on a single computer or processor, but can be distributed in a modular fashion amongst a number of different computers or processors to implement various aspects of the systems and methods disclosed herein.

Thus, illustrative embodiments and arrangements of the present systems and methods in part, provide a computer implemented method, a computer-based system, and/or a computer program product for inspecting insulated equipment for corrosion. The flowchart and block diagrams in the figures illustrate the architecture, functionality, and operation of possible implementations of systems, methods and computer program products according to various embodiments and arrangements. In this regard, each block in the flowchart or block diagrams can represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprising" and/or "comprises", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present disclosure, which is set forth in the following claims.

What is claimed is:

1. A method for detecting corrosion under insulation within insulated equipment using at least one device supporting an infrared detector and at least one pulsed eddy current (PEC) sensor, the method comprising:
   detecting, at one or more locations along the insulated equipment with the infrared detector, infrared waves emitted from the insulated equipment;
   developing, using the infrared waves detected by the infrared detector, at least one image of an inner surface of the insulated equipment at the one or more locations based on the detected infrared waves;
   determining, using a processor configured by code executing therein, at least one area that is susceptible to corrosion under insulation based on the at least one developed image;
   storing positioning data corresponding to the at least one susceptible area in a database;
   returning the device to the at least one susceptible area based on the stored positioning data;
   inspecting, with the at least one PEC sensor, the at least one susceptible area on the insulated equipment, wherein the step of inspecting comprises:
   generating a magnetic field,
   penetrating a metallic jacket of the insulated equipment with the generated magnetic field to magnetize an inner wall of the equipment, thereby inducing an eddy current in the inner wall, and
   monitoring a decay in strength of the eddy current over time; and
   determining, using the processor configured by code executing therein, whether any corrosion under insulation exists at the at least one susceptible area based on a rate of the decay in strength of the eddy current.

2. The method of claim 1, further comprising the step of:
   testing the one or more locations along the insulated equipment using an infrared gas detector operatively connected to the device, for gas emissions indicative of corrosion under insulation.

3. The method of claim 1, wherein the at least one device is an unmanned aerial vehicle.

4. The method of claim 3, wherein the unmanned aerial vehicle includes aerial and ground locomotive capabilities.

5. The method of claim 1, wherein the at least one device is selected from the group consisting of an unmanned aerial vehicle, a control station, a mobile robot, and a handheld device.

6. The method of claim 1, wherein the positioning data is global positioning data.

7. The method of claim 1, wherein the positioning data is relative positioning data.

8. The method of claim 1, further comprising the step of:
   implementing a quiescent period after detection of the insulated equipment with the infrared detector and prior to inspection of the susceptible area with the at least one PEC sensor.

9. A method for detecting corrosion under insulation within insulated equipment using at least one modular unmanned aerial vehicle (UAV) having aerial and ground locomotive capabilities, the method comprising:
   installing an infrared module on the at least one UAV, wherein the infrared module comprises an infrared detector;
   positioning the UAV on the insulated equipment;
   detecting, at one or more locations along the insulated equipment with the infrared detector, infrared waves emitted from the insulated equipment;
   developing, using the infrared waves detected by the infrared detector, at least one image of an inner surface of the insulated equipment at the one or more locations based on the detected infrared waves;
   determining, using a processor configured by code executing therein, at least one area that is susceptible to corrosion under insulation based on the at least one developed image;
   installing a pulsed eddy current (PEC) module on the at least one UAV, wherein the PEC module comprises at least one PEC sensor;
   inspecting, with the at least one PEC sensor, the at least one susceptible area on the insulated equipment, wherein the step of inspecting comprises:
   generating a magnetic field,
   penetrating a metallic jacket of the insulated equipment with the generated magnetic field to magnetize an inner wall of the equipment, thereby inducing an eddy current in the inner wall, and
   monitoring a decay in strength of the eddy current over time; and
   determining, using the processor configured by code executing therein, whether any corrosion under insulation exists at the at least one susceptible area based on a rate of the decay in strength of the eddy current.

10. The method of claim 9, further comprising the steps of:
    storing positioning data corresponding to the at least one susceptible area in a database; and
    returning the UAV to the at least one susceptible area based on the stored positioning data.

11. The method of claim 9, wherein the step of installing the PEC module comprises uninstalling the infrared module.

12. The method of claim 9, wherein the step of positioning the UAV comprises:
    attaching the UAV to the insulated equipment via a clamping mechanism housed on the UAV.

13. The method of claim 9, further comprising the steps of:
    installing an infrared gas module on the at least one UAV, wherein the infrared gas module comprises an infrared gas detector; and testing the at least one location on the insulated equipment, using the infrared gas detector, for gas emissions indicative of corrosion under insulation.

14. The method of claim 9, further comprising the step of:
implementing a quiescent period after detection of the insulated equipment with the infrared detector and prior to inspection of the susceptible area with the at least one PEC sensor.

15. An autonomous, modular unmanned vehicle having aerial and ground locomotive capabilities for inspection of insulated equipment for corrosion under insulation, the vehicle comprising:
a controller, having a memory storing instructions in the form of code and a processor configured by executing the instructions therein, wherein the controller is configured to enable operations of the vehicle;
a power source configured to power all components of the vehicle;
an infrared module comprising an infrared detector, wherein the infrared detector is configured to detect infrared waves emitted from the insulated equipment and to develop an image of the inner wall of the insulated equipment at one or more locations based on the detected infrared waves, and wherein the infrared module is selectively removable from the vehicle;
a pulsed eddy current (PEC) module comprising at least one PEC sensor, wherein the at least one PEC sensor is configured to induce an eddy current in the inner wall and monitor a decay in strength of the eddy current over time, and wherein the PEC module is selectively removable from the vehicle;
a clamping mechanism configured to selectively attach the vehicle to the insulated equipment; and
at least one pair of wheels configured to move the vehicle along an outer surface of the insulated equipment when the vehicle is attached to the insulated equipment via the clamping mechanism.

16. The vehicle of claim 15, further comprising:
at least one of an infrared gas detector, a positioning module, a depth sensor, an inertia measurement unit, and a LIDAR device.

17. The vehicle of claim 15, wherein the power source is a battery.

18. The vehicle of claim 17, further comprising:
a power receiver operatively connected to the battery, wherein the power receiver is configured to wirelessly transfer power from a remote power source to the battery.

19. The vehicle of claim 15, wherein the at least one pair of wheels are configured to move the vehicle longitudinally along the outer surface of the insulated equipment.

20. The vehicle of claim 15, wherein the at least one pair of wheels are omniwheels configured to enable omnidirectional locomotion along the outer surface of the insulated equipment.

21. A system for inspection of insulated equipment for corrosion under insulation, comprising:
at least one autonomous, modular unmanned vehicle having aerial and ground locomotive capabilities, wherein the vehicle comprises:
a controller, having a memory storing instructions in the form of code and a processor configured by executing the instructions therein, wherein the controller is configured to enable operations of the vehicle,
a battery configured to power all components of the vehicle,
a power receiver operatively connected to the battery,
at least one of an infrared module and a pulsed eddy current (PEC) module, wherein the infrared module comprises an infrared detector configured to detect infrared waves emitted from the insulated equipment and to develop an image of the inner surface of the insulated equipment at one or more locations based on the detected infrared waves, and the infrared module is selectively removable from the vehicle, and wherein the PEC module comprises at least one PEC sensor configured to induce an eddy current in the inner wall and monitor a decay in strength of the eddy current over time, and the PEC module is selectively removable from the vehicle, and
a clamping mechanism configured to selectively attach the vehicle to the insulated equipment, and
at least one pair of wheels configured to move the vehicle along the equipment; and
a control station comprising a power source and a power transmitter, wherein the power transmitter is configured to wirelessly transfer power from the power source to the power receiver of the at least one vehicle.

22. The system of claim 21, wherein the at least one vehicle comprises a first vehicle comprising the infrared module and a second vehicle comprising the PEC module.

* * * * *